US008219373B2

(12) United States Patent
Fontes et al.

(10) Patent No.: US 8,219,373 B2
(45) Date of Patent: Jul. 10, 2012

(54) SYSTEM AND METHOD FOR GRAPHICALLY CREATING MODELS FOR SIMULATING SYSTEMS OF REACTING SPECIES

(75) Inventors: Eduardo Fontes, Vallentuna (SE); Henrik von Schenck, Nacka (SE); Ottmar Raeymaeckers, Nacka (SE); Phillip Byrne, Hagersten (SE); Lars Langemyr, Stockholm (SE); Michael Frenklach, Orinda, CA (US)

(73) Assignee: Comsol AB, Stockholm (SE)

( * ) Notice: Subject to any disclaimer, the term of this patent is extended or adjusted under 35 U.S.C. 154(b) by 1155 days.

(21) Appl. No.: 11/206,919

(22) Filed: Aug. 19, 2005

(65) Prior Publication Data

US 2007/0043546 A1    Feb. 22, 2007

(51) Int. Cl.
*G06G 7/58* (2006.01)
(52) U.S. Cl. .................................. 703/12; 703/2; 703/11
(58) Field of Classification Search .................... None
See application file for complete search history.

(56) References Cited

U.S. PATENT DOCUMENTS

| 5,625,579 | A  | * | 4/1997 | Hinsberg et al. | ................. | 703/12 |
| 2005/0042663 | A1 | * | 2/2005 | Blinov et al. | .................... | 703/11 |
| 2005/0187717 | A1 |   | 8/2005 | Paxson et al. | | |
| 2005/0187746 | A1 | * | 8/2005 | Hicklin et al. | ................... | 703/11 |
| 2005/0187747 | A1 |   | 8/2005 | Paxson et al. | | |

OTHER PUBLICATIONS

Hillewaert et al. (AIChE Journal, vol. 34, No. , p. 17-24, Jan. 1988).*
Prickett et al. (Computers chem. Engng vol. 21, No. 11, pp. 1219-1235, 1997).*
Cardinali et al. (Industrial Management + Data Systems. 1994. vol. 94, Iss. 4; p. 3, 5 pgs.).*
Andrews et al. (Phys. Biol., vol. 1, p. 137-151, Aug. 12, 2004).*
Broadbelt et al. (Ind. Eng. Chem. Res., vol. 33, No. 4, p. 790-799, 1994).*
Of Beard et al. (Biophysical Journal vol. 83 Jul. 2002 79-86).*
Bruaset et al. (A comprehensive set of tools for solving partial differential equations; DIFFPACK. In: Daehlen, M; Tveito, A. (eds.), Numerical Methods and Software Tools in Industrial Mathematics, Brinkhauser Boston, Boston, MA, pp. 61-90, 1997).*
Oh et al. (Computers Chem. Engng., vol. 20, No. 6/7, p. 611-633, 1996).*
Kurata et al. (Genome Res., vol. 15, p. 590-600, Apr. 2005).*
BIOSOFT.RU, "BioUML Overview," (Copyright © 2001-2004) PowerPoint presentation, at http://www.biouml.org/presentations.shtml.
BIOSOFT.RU, "What is BioUML?" (Copyright © 2001-2004) at http://www.biouml.org.
The Systems Biology Institute, "Cell Designer™: A Modeling Tool of Biochemical Networks," (Copyright © 2004-2005) at http://celldesigner.org.
Bioinformatics Institute, "Cellware: A New Modeling and Simulation Tool for Modeling Cellular Transactions," (Copyright © 2003-2005) at http://www.bii.a-star.edu/sg/achievements/applications/cellware/.
Kyusyu Institute of Technology, "CADLIVE," (Copyright © 2003) at http://kurata21.bse.kyutech.ac.jp/cadlive/.
INSILICO Biotechnology, "INSILICO Software," (Copyright © 2005) at http://www.insilico-biotechnology.com/f_products.html.
BIOCHAM, "The Biochemical Abstract Machine BIOCHAM," at http://contraintes.inria.fr/BIOCHAM/.
COPASI, "Complex Pathway Simulator," at http://www.copasi.org/tiki-index.php.
Institute for Systems Biology, "Dizzy," at http://labs.systemsbiology.net/bolouri/software/Dizzy?.
Pedro Mendes, "Gepasi: Biochemical Simulation," (Copyright © 1996-2004) at http://www.gepasi.org.
AEA Technology, "Material and Chemical Process Assessment. Industrial Application for Kinetics and Chemical Thermodynamics," (Copyright © 2000) at http://www.aeat.co.uk/mcpa/areas/software/facsimil/facsapps/radio.htm.
ESM Software, "SimuSage" (Copyright © 2001-2005) at http://www.esm-software.com/simusage/.
Ohio Supercomputer Center (OSC), "WebEd Education Outreach & Training. Modeling Chemical Kinetics with Stella," (Copyright © 2006) at http://www.osc.edu/education/webed/Projects/chemical_kinetics/index.shtml.
Starting Point, "What is Stella II," at http://serc.carleton.edu/introgeo/mathstatmodels/UsingStellaII.html.
Berkeley Madonna, "Modeling and Analysis of Dynamic Systems," (Copyright © 1993-2001) at http://www.berkeleymadonna.com.
ReactionLab, "ReactionLab," at http://reactionlab.sourceforge.net/.
Frenklach & Nokleberg, "Reaction Lab. A Problem Solving Environment for Modeling Reaction Kinetics," Poster Presentation at 29$^{th}$ *International Symposium on Combustion*, Sapporo, Japan, Poster No. 19-1419 (Jul. 21-26, 2002).
Gas Research Institute (GRI), "GRI-Mech Calculator 3.0," at http://diesel.me.berkeley.edu/~gri_mech/cal30/demo11/index.html.
James C. Ianni, "Kintecus Home," (Copyright © 2006) at http://www.kintecus.com/.
CADLIVE Ver. 2.15 Operation Manual, Kyushu Institute of Technology, 36 pages (appears to be dated Mar. 2004).
CADLIVE Text Editor Version 2.15, 24 pages (dated sometime prior to Jan. 27, 2012).
Commentary and Instruction for CHECKDAE, Mathematical Equation Conversion System for User Function Creation, 7 pages (dated sometime prior to Jan. 27, 2012).

(Continued)

*Primary Examiner* — Karlheinz R Skowronek
(74) *Attorney, Agent, or Firm* — Nixon Peabody LLP

(57) ABSTRACT

A system and method for generating a model for simulating systems of reacting species comprising receiving a plurality of reaction formulas, determining a reaction rate expression for each of the received reaction formulas, and generating a model for simulating systems of reacting species using the received reaction formulas and the determined reaction rate expressions. The invention further relates to pruning the reaction list to deactivate one or more reactions in the reaction list based on one or more criteria, such as threshold criteria. A graphical user interface may also be used in connection with the present invention in various ways. An output based on the generated model may be displayed, wherein the output displays the composition and temperature dependence of the system of reacting species. Material and energy balances may also be generated for the reacting species as input to a solver of partial differential equations.

69 Claims, 10 Drawing Sheets

OTHER PUBLICATIONS

Commentary and instruction for merging parameters (mergeParams), 3 pages (dated sometime prior to Jan. 27, 2012).

Commentary for PARSEDAE, Conversion of regulator-reaction equations into mathematical equations, 18 pages (dated sometime prior to Jan. 27, 2012).

CADLIVE Ver. 2.15 Operation Manual, Kyushu Institute of Technology, 37 pages (appears to be dated Mar. 2004).

Hiroyki Kurata, Nana Matoba and Natsumi Shimizu, "CADLIVE for constructing a large-scale biochemical network based on a simulation-directed notation and its application to yeast cell cycle", Nucleic Acids Research, 2003, vol. 31, No. 14 4071-4084, DOI: 10.1093/nar/gkg461, 14 pages (2003).

Instruction for CADLIVE Simulator, 22 pages (dated sometime prior to Jan. 27, 2012).

Instruction for installing CADLIVE Simulator, 10 pages (dated sometime prior to Jan. 27, 2012).

Instruction for PARSEDAE, 12 pages (dated sometime prior to Jan. 27, 2012).

CADLIVE Ver. 2.15 Operation Manual, Kyushu Institute of Technology, 37 pages (appears to be dated Apr. 2004).

\* cited by examiner

SYSTEM AND METHOD FOR GRAPHICALLY CREATING MODELS FOR SIMULATING SYSTEMS OF REACTING SPECIES

FIELD OF THE INVENTION

This invention relates to a system and method for graphically creating models for simulating systems of reacting species. More particularly, the invention relates to a system and method for receiving and simulating chemical reactions and transport.

BACKGROUND

Certain types of reaction simulators known in the art operate by receiving a set of chemical reactions formulas and information about these formulas through data files of specific format. For example, CHEMKIN, a software package from Sandia National Labs, is able to interpret the data in these files and generate reacting species balance equations. ReactionLab, developed by Professor Michael Frenchlach at the University of California, Berkeley, is also able to interpret the data files containing reaction formulas and information. Because this is done by parsing the information in data files of specific formats, the information about reaction thermodynamics, reaction kinetics, and transport properties has to be included in such file using a specific syntax.

SUMMARY

The present invention relates to a system and method for generating a model for simulating systems of reacting species comprising receiving a plurality of reaction formulas, determining a reaction rate expression for each of the received reaction formulas, and generating a model for simulating systems of reacting species using the received reaction formulas and the determined reaction rate expressions. A reaction list of at least one reaction for at least one of the received reaction formulas may be generated. Also, the at least one reaction rate expression associated with one or more reactions in the reaction list at equilibrium may be eliminated, for example, based on one or more threshold criteria. Furthermore, at least one thermodynamic property and at least one kinetic property of each reaction in the reaction list may be determined. Additionally, a species list based on the received reaction formulas may be generated. At least one thermodynamic property and at least one transport property may also be determined for each species in the species list. Furthermore, at least one time dependent term and at least one concentration for at least one species at steady-state may be eliminated.

The present invention further relates to pruning the reaction list to deactivate one or more reactions in the reaction list based on one or more criteria, such as threshold criteria. A user may modify the one or more criteria via a graphical user interface.

A graphical user interface may be used in connection with the present invention in various ways. For example, the reaction formulas may be received via a graphical user interface, the generated model may be displayed on a graphical user interface, the determined reaction rate expression may be modified via a graphical user interface, the generated reaction list may be displayed in a graphical user interface, and the generated species list may be displayed in a graphical user interface.

Also, an output based on the generated model may be displayed, wherein the output displays the composition and temperature dependence of the system of reacting species. In addition, material and energy balances may be generated for the reacting species as input to a solver of partial differential equations.

The system of the present invention uses one or more of a receiving system, a reaction rate determination system, a model generating system, a display system, a reaction list generating system, an elimination system, a reaction property determination system, a pruning system, a species list generating system, a species property determination system, a material and energy balances generating system, and the like to implement the present invention.

The present invention also relates to a computer readable medium having instructions stored thereon for generating a model for simulating systems of reacting species, which when executed by a processor, cause the processor to carry out the steps necessary to implement the methods of the present invention, including, for example, receiving a plurality of reaction formulas, determining a reaction rate expression for each of the received reaction formulas, and generating a model for simulating systems of reacting species using the received reaction formulas and the determined reaction rate expressions. The medium may also include instructions for carrying out any of the other steps described herein with respect to the methods of the present invention.

Thus, the present invention provides a system and method for graphically creating models for simulating systems of reacting species. The user can type-in, or otherwise input reaction formulas directly into a graphical user interface. These formulas are then parsed and used to create reaction rate expressions for each of the reaction formulas. In addition, a reaction and species list is also defined, and reaction rate expressions are automatically attributed to each of the species involved in the reaction formulas. The reaction rate expressions may also be modified by a user by overwriting the automatically generated expressions. Different assumptions about reactions and species in the system for specifying equilibrium reactions, steady-state, and constant concentration may also be selected by a user and new reaction rate expressions accounting for the user's modifications may be automatically computed. Furthermore, thermodynamic and transport properties, as functions of temperature and composition, may also be automatically computed for a system of reacting species using a minimum of input in a graphical user interface. An output of material and energy balances may also be generated and sent to a solver of partial differential equations.

DETAILED DESCRIPTION

As is described herein and illustrated by the accompanying figures, the present invention relates to a system and method for generating a model for simulating systems of reacting species comprising receiving a plurality of reaction formulas, determining a reaction rate expression for each of the received reaction formulas, and generating a model for simulating systems of reacting species using the received reaction formulas and the determined reaction rate expressions.

Figure 1:
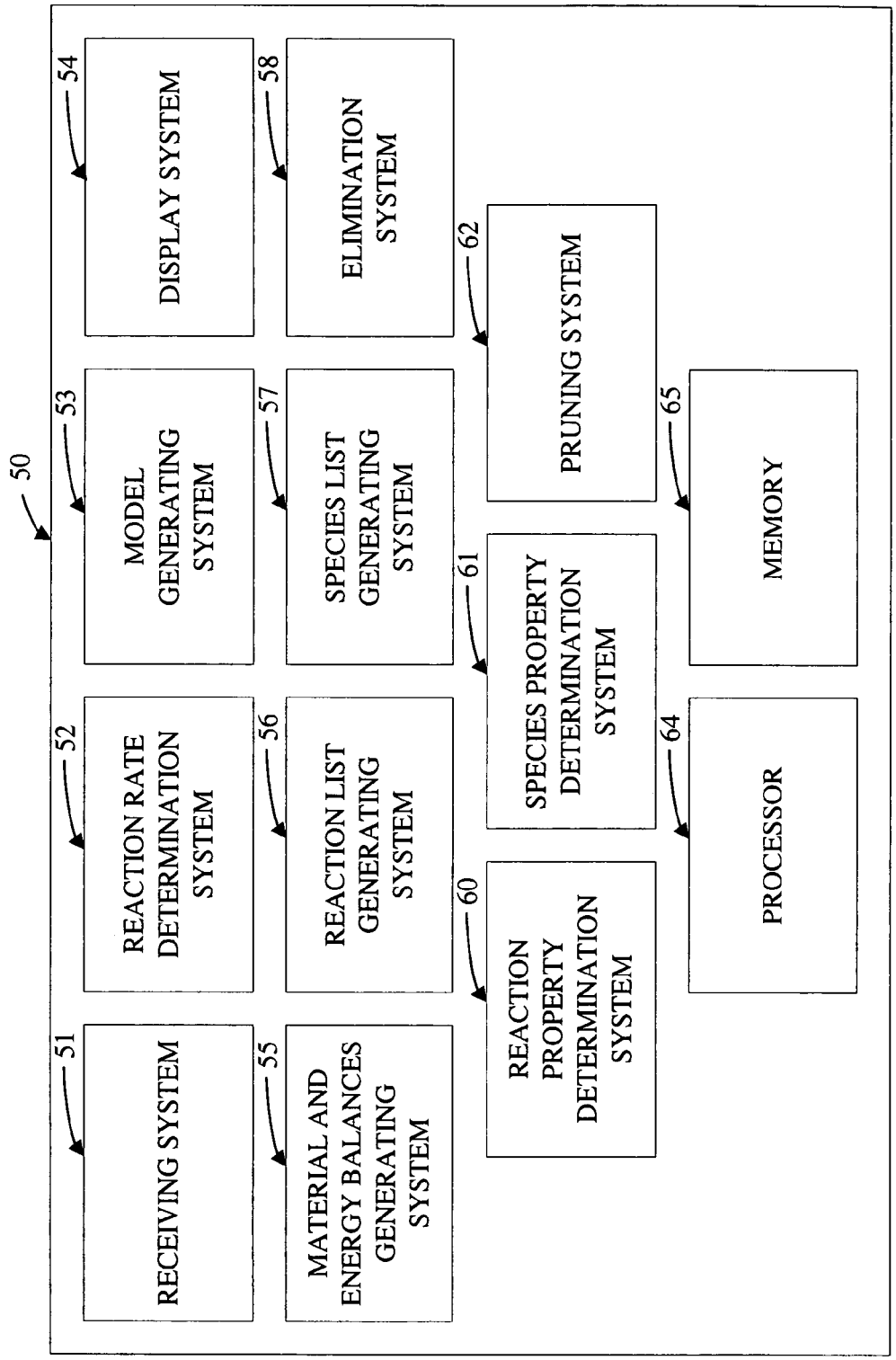
FIG. 1 shows an exemplary system of the present invention.

Referring to FIG. 1, an exemplary system 50 of the present invention is illustrated. System 50 includes a receiving system 51, a reaction rate determination system 52, a model generating system 53, a display system 54, a materials and energy balances generating system 55, a reaction list generating system 56, a species list generating system 57, an elimination system 58, a reaction property determination system 60, a species property determination system 61, a pruning system 62, a processor 64, and a memory 65, as well as any other suitable systems or components, although system 50 could include other numbers and types of elements in other configurations.

Generally, system 50 is a system for generating a model for simulating systems of reacting species. According to an embodiment of the present invention, receiving system 51 receives a plurality of reaction formulas, reaction rate determination system 52 determines a reaction rate expression for each of the received reaction formulas, and model generating system 53 generates a model for simulating systems of reacting species using the received reaction formulas and the determined reaction rate expressions. In addition, reaction list generating system 56 generates a reaction list of at least one reaction for at least one of the received reaction formulas. Reaction property determination system 60 determines at least one thermodynamic property and at least one kinetic property of each reaction in the reaction list. Pruning system 62 prunes the reaction list to deactivate one or more reactions in the reaction list based on one or more criteria. Species list generating system 57 generates a species list based on the received reaction formulas. Species property determination system 61 determines at least one thermodynamic property and at least one transport property for each species in the species list. Material and energy balances generating system 55 generates material and energy balances for the reacting species as input to a solver of partial differential equations. Elimination system 58 eliminates at least one reaction rate expression associated with one or more reactions in the reaction list at equilibrium, at least one time dependent term for at least one species at steady-state, and at least one concentration for at least one species at constant concentration. Display system 54 displays the generated model, the generated reaction list, and the species list in a graphical user interface, and displays an output based on the generated model, wherein the output displays the composition and temperature dependence of the system of reacting species.

The methods and systems of the present invention may be implemented on any suitable computer system or computing device. For example, the present invention may be implemented on workstations, PCs, laptop computers, PDAs, hand-held devices, cellular telephones, wireless devices, other computerized devices, and the like. It is to be understood that the devices and systems of the exemplary embodiments are for exemplary purposes, as many variations of the specific hardware used to implement the exemplary embodiments are possible, as will be appreciated by those skilled in the relevant art(s).

Furthermore, the methods and systems of the exemplary embodiments may be conveniently implemented using one or more general purpose computer systems, microprocessors, digital signal processors, micro-controllers, and the like, programmed according to the teachings of the exemplary embodiments of the present invention, as will be appreciated by those skilled in the computer and software arts.

In addition, two or more computing systems or devices can be substituted for any one of the devices and systems of the exemplary embodiments. Accordingly, principles and advantages of distributed processing, such as redundancy, replication, and the like, also can be implemented, as desired, to increase the robustness and performance the devices and systems of the exemplary embodiments.

The present invention may also be implemented on computer systems that extend across any network using any suitable interface mechanisms and communications technologies including, for example, telecommunications in any suitable form (e.g., voice, modem, and the like), wireless communications media, wireless communications networks, cellular communications networks, G3 communications networks, Public Switched Telephone Network (PSTNs), Packet Data Networks (PDNs), the Internet, intranets, a combination thereof, and the like.

The present invention may also be embodied as a computer readable medium having instructions stored thereon for generating a model for simulating systems of reacting species, which when executed by a processor, cause the processor to carry out the steps necessary to implement the methods of the present invention. The medium may also include instructions for carrying out any of the other steps described herein with respect to the methods of the present invention.

Figure 2:
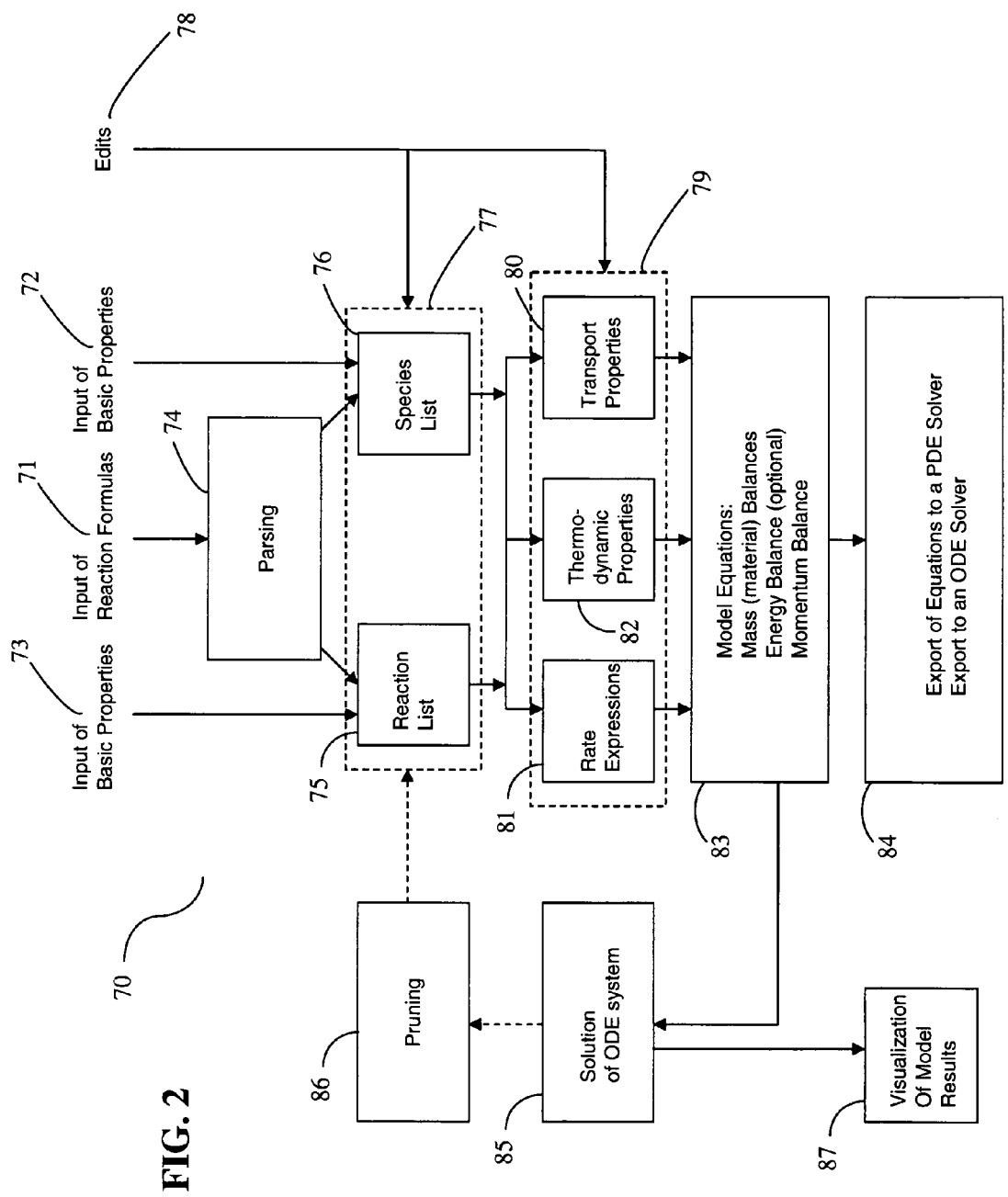
FIG. 2 shows an exemplary method of the present invention.
Figure 3:
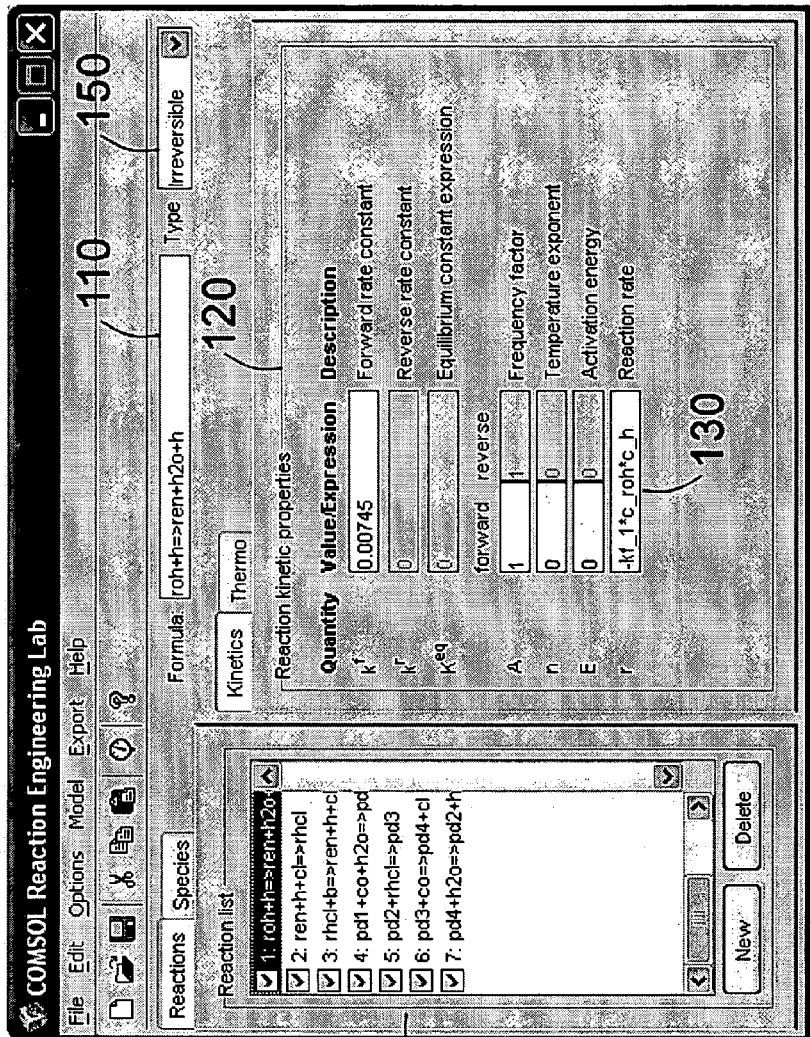
FIG. 3 shows a graphical user interface for reaction formula inputting.

An exemplary method 70 of an embodiment of the present invention is illustrated in FIG. 2, although methods with other numbers and types of steps could be used. At step 71, reactions formulas are input into the receiving system 51 in the system 50. In this particular embodiment, an exemplary graphical user interface 100 in the display system 54 for the system 50 is used to input reaction formulas into the receiving system 51 as shown in FIG. 3, although other manners for entering the reaction formulas could be used. More specifically, the graphical user interface 100 includes a reaction formula edit field 110 in which new reaction formulas may be entered or existing reaction formulas may be edited. For example, a user using a mouse and a keyboard can input new reaction formulas or edit existing reaction formulas in reaction formula edit field 110.

The graphical user interface 100 also includes a reaction kinetics properties page 120 for inputting and displaying kinetic properties, a reaction rate field 130 for editing and displaying reaction rate expressions, and a reaction type list box 150, although the graphical user interface 100 could have other numbers and types of fields. Reaction kinetics properties page 120 includes a plurality of fields including kinetic and thermodynamic information. For example, reactions kinetics properties page 120 may include fields for the forward rate constant ($k^f$), the reverse rate constant ($k^r$), the equilibrium constant expression ($K^{eq}$), forward and reverse fields for frequency factor (A), temperature exponent (n), and activation energy (E), and reaction rate (r).

Reaction rate field 130 is displayed in a manner that enables editing of the displayed reaction rate expression. The displayed reaction rate (r) corresponds to the selected reaction formula displayed in reaction list 140 and in formula edit field 110. Any of the rate expressions in reaction rate field 130 may be modified by overwriting it to input any other reaction rate expression using the notations automatically generated by the system for the species involved in the system of reacting species. For example, a user can edit reaction rate expression field 130 by entering "-kf_1*c_h", thus changing the reaction order of the selected reaction to first order and only dependent on the concentration of species labeled "h". Any expression of "c_h" or any other species concentration label can be used for the manual input of reaction rate expressions. The possibility to manually define reaction rate expressions as analytical functions of the concentration of the automatically parsed species in a reaction formula in a graphical interface gives the user improved control over the reaction rate expressions.

Referring back to FIG. 2, in step 72 the operator of the system 50 can input one or more properties to be used in determining the species list. Additionally, in step 73 the operator of the system 50 can input one or more properties to be used in determining the reaction list.

In step 74, the reaction formulas input into system 50 are parsed. The direct manual input and automatic parsing of reaction formulas to automatically generate reaction rate expressions as provided by the present invention enables a user to have improved control over the modeling process of the present invention. For example, assume a reaction formula, A+B=>C, is input directly into the graphical user interface using an intuitive syntax. The reaction formula, A+B=>C, is then automatically parsed, and the formation of C from A and B is identified as an irreversible reaction. The delimiters, "+" and "=>", separate the species, and the parser uses the delimiter symbols to gain the information needed to derive the rate expression. The kinetic rate expression is then automatically computed by default from the reaction formula using the mass action law. In the example of A+B=>C, the reaction rate expression is $r=k_f*c_A*c_B$ according to the mass action law, where $k_f$ is the rate constant for the forward reaction, $c_A$ and $c_B$ are the concentrations of species A and B, respectively. As is shown in FIG. 3, a user may edit any of these fields as necessary to customize the results.

The mass action law is not always applicable to a reaction formula. For example, a reaction can comprise several intermediate steps involving intermediate species that are not included in the reaction formula. For this reason, the user is allowed to overwrite the automatically generated reaction rate expressions. The method will parse the new rate expression typed-in by the user by identifying the notations for the rate constants and species concentrations. This "editable form" refers to the fact that the field for the rate expression is both a displaying and an edit field.

In addition, the reactions may be labeled, and all expressions related to this reaction may be labeled as well. When this occurs, reaction rate field 130 is labeled accordingly. If the reaction formula in reaction formula edit field 110 corresponds to reaction labeled "1" then the reaction rate edit field 130 is labeled "r_1" by the system. The expressions "r_1" can be used in other parts of the system to refer back to the rate expression for reaction formula labeled "1". The label remains unchanged even if reactions are removed from the model. The possibility of labeling and referring back to expressions in the edit fields in the reaction page is very advantageous. For example, a user can type "r_1" in the reaction rate field corresponding to reaction labeled "7", thus overwriting the automatically generated rate expression, and the system will understand that the user wants to set the reaction rate for reaction 7 equal to that of the previously defined reaction 1.

The fact that the method labels different reactions is very advantageous for the user. For example, a change made by a user in an edit field for a chemical reaction automatically updates the labeled entities used in other parts of the systems, thus saving the user from tedious manual changes every time a reaction mechanism is changed.

In addition, according to an embodiment of the present invention, reaction rate terms in the material balances, which describe the system of reacting species, may be eliminated when using equilibrium assumptions. In this regard, a linear combination of the material balances, in the model of a system of reacting species, may be automatically computed in order to eliminate the reaction rate terms for reactions that are in equilibrium. The linear combination of n material balances leads to n-m material balance combinations where m is the number of reactions at equilibrium. The remaining m equations required to properly generate the model are provided using the corresponding equilibrium equations.

The possibility to eliminate reaction rate terms for reactions in equilibrium directly in a graphical user interface is very advantageous. It greatly simplifies the treatment of reactions that are substantially faster than others in a reacting system. The treatment of equilibrium reactions can be very important when setting up a model for the reaction kinetics in a system. The forward and backward reaction in an equilibrium reaction can be extremely fast, giving reaction rate terms that are extremely large compared to other non-equilibrium reactions. In the numerical solution of the concentration, temperature, and reaction rates in a system, these large reaction rates can lead to numerical instability. This instability can be avoided by eliminating the reaction rate expressions for the equilibrium reaction. This is exemplified in the procedure below.

Assume the reaction A=B exists at equilibrium in a given system. The rate expression for this reaction would be $r=k_f*c_A-k_b*c_B$ according to the mass action law. The corresponding material balances for species A and B would then be expressed as:

$$\frac{\partial c_A}{\partial t} + \nabla \cdot N_A + k_f c_A - k_b c_B = 0$$

$$\frac{\partial c_B}{\partial t} + \nabla \cdot N_B - k_f c_A + k_b c_B = 0$$

where $N_A$ and $N_B$ denote the flux vectors of species A and B, respectively, which in turn are functions of the concentrations $c_A$ and $c_B$. The reaction rate expressions in the above mass balances are eliminated by mathematical calculations. In the above case, it is obvious that the two equations should be added to give:

$$\frac{\partial c_A + c_B}{\partial t} + \nabla \cdot (N_A + N_B) = 0.$$

However, this yields one equation and two unknowns ($c_A$ and $c_B$). The second equation needed to solve the system is yielded by using the equilibrium expression:

$$\frac{c_B}{c_A} = K_{eq}$$

This is generally achieved, which implies that an equilibrium reaction can have an arbitrary number of species, with the elimination involving the corresponding number of mass balances.

Figure 4:
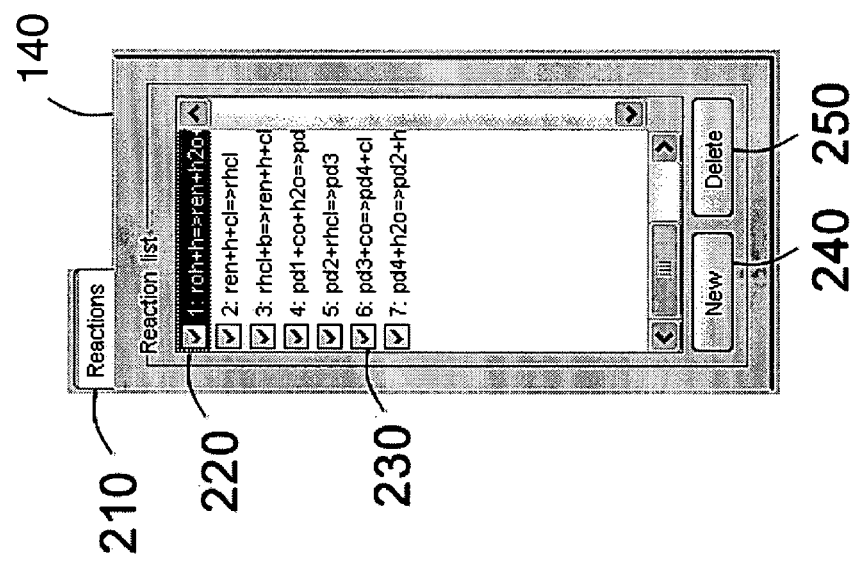
FIG. 4 shows a reaction list produced by the method of the invention.

In step 75, a list of reactions is produced by the reaction list generating system 56 from the parsed input reaction formulas and these reactions are illustrated in the reaction page 140 shown in FIGS. 3 and 4. The reaction page 140, which is also referred to as reaction list 140, includes a reaction tab 210, a reaction selection 220, an active reaction checkbox 230, a new reaction button 240, and a delete reaction button 250, although the reaction page 140 can include other types and numbers of elements in other configurations. Reaction tab 210 may be selected by a user to select reaction page 140. Reaction selection 220 indicates one or more reactions that are selected by a user, for example, by clicking on specific reactions with the mouse. The user can modify the selected reaction via the graphical user interface 100. Active reaction checkbox 230 is a toggle box that may be checked for manual or automatic activation and deactivation of reactions in reaction list 140. A reaction may be deactivated by unchecking active reaction checkbox 230 or by an automatic pruning process, as described in more detail below. When deactivated, a reaction will not be part of the model for simulating systems of reacting species. Species that exclusively take part in the deactivated reaction formula are also removed from the model. The "New" and "Delete" buttons 240 and 250 are used to add or delete reactions from reaction list 140, although other numbers and types of buttons could be used.

Referring back to FIG. 2, in step 86 the pruning process of the present invention automatically deactivates one or more reactions in reaction list 140. The reactions to be deactivated are selected based on an estimation of the magnitude of the reaction rate for each reaction and by using a relative threshold for the smallest reaction rate that should be included in the model of the system of reacting species. The use of pruning simplifies the modeling process. In addition, the user is given more control by allowing the user to visualize and modify the pruning process as needed. The ability to automatically prune the reaction list and to enable a user to specify the pruning criteria directly in a graphical user interface is very advantageous.

Pruning can be done in a number of different fashions. One example is the use of the relative magnitude of a reaction in a reacting system. If a reaction has a rate smaller than a given fraction of a measuring reaction, then this reaction is removed from the model. For example, assume that species A can react in two different reactions:

$A+B =>C$ $A+D =>E$ which results in the following mass (material) balance for species A:

$$\frac{\partial c_A}{\partial t} + \nabla \cdot N_A + k_{f,1} c_A c_B + k_{f,2} c_A c_D = 0.$$

If the first reaction is used as reference, then the rate of the second reaction can be measured as a fraction of the first one:

$$\frac{k_{f,2} c_A c_D}{k_{f,1} c_A c_B} = \text{fraction.}$$

If this fraction is smaller than a threshold $\epsilon$, then the second reaction is removed from the model. If the second reaction is neglected, using automatic pruning, then the automatically computed mass (material) balance for A becomes:

$$\frac{\partial c_A}{\partial t} + \nabla \cdot N_A + k_{f,1} c_A c_B = 0.$$

For a very small $\epsilon$, the contribution of the second reaction to the consumption of A is negligible. This also implies that the species that only take part in the second reaction are removed from the model (their mass balances are removed). The reactions contribution to the energy balance is also removed.

Another possible pruning strategy is to prune based on concentrations. For example, if the relative concentration of a species is smaller than that of a measuring species, then the mass balance for this species may be removed from the model.

Figure 5:
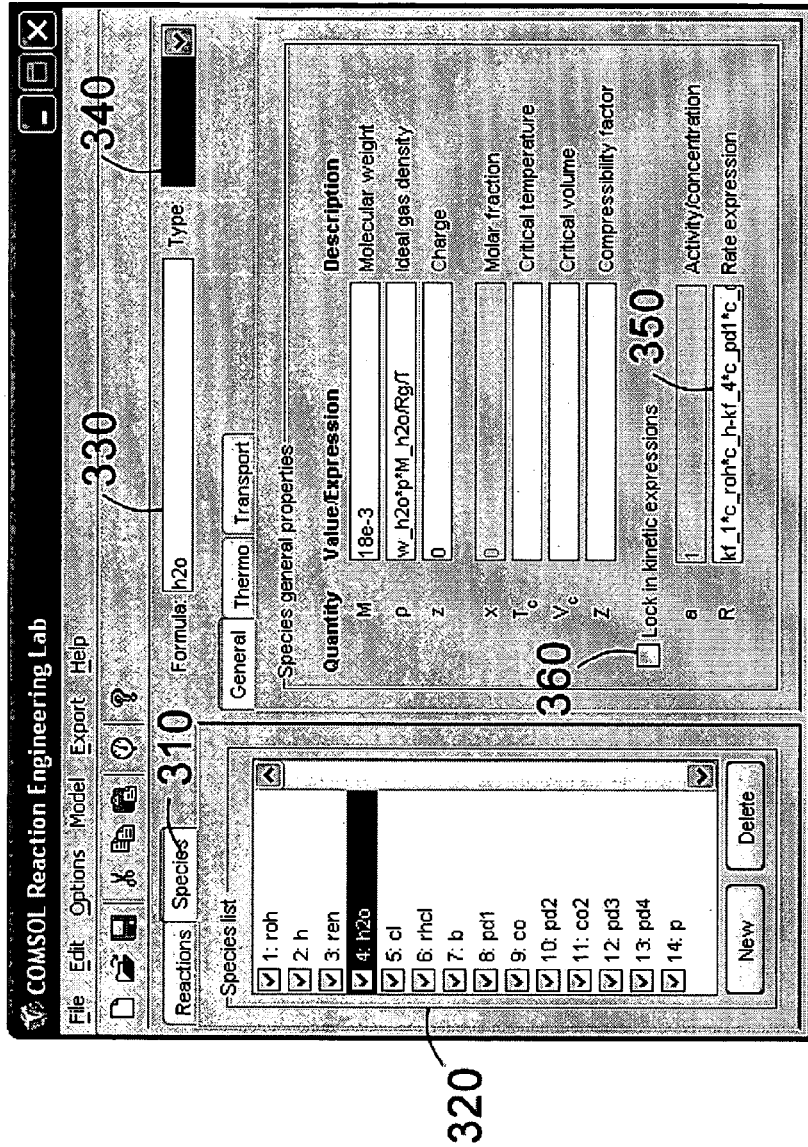
FIG. 5 shows a graphical user interface in species view, automatically created by the method of the invention from the reaction formulas.

In step 76, a list of species also is automatically generated by the species list generating system 57 based on the parsed input reaction formulas included in reaction page 140 shown in FIG. 3. To display this list of species, the species tab next to the reactions tab at the top of the reactions page 140 in the graphical user interface 100 is selected by the user using a mouse or other input device. When the species tab 310 is selected, the graphical user interface 300 shown in FIG. 5 is displayed by the display system 54 of the system 50.

Each species in species list 320 is uniquely labeled according to the formula in species formula edit field 330. In species formula edit field 330, species labeled "h2o" automatically generates other entities and properties labeled accordingly, for example the concentration of "h2o" is labeled "c_h2o". The expressions in the graphical user interface 300 are labeled correspondingly and can be used by a user by typing such an expression in other parts of the graphical user interface. For example, the method labels rate expression 350 to "r_h2o" since it is associated to species h2o. When a user types "r_h2o" in the rate expression edit field for species labeled "cl", thus overwriting the automatically generated rate expression for cl, the system understands that rate expression "r_cl" should be equal to that of "r_h2o", in this case setting the reaction rate for cl equal to that of h2o. This gives the user the ability to dynamically relate the selected reaction or species to other reactions and concentrations, or any other entity labeled in that step. This grants that the modification of a reacting system is made consistently upon a modification in one reacting step.

In addition, the species type may be specified in species type list 340. A user can select a species type as steady-state or solvent by using species list 340, which modifies the default definition of a species in a model. In the former, the time derivative of the species concentration, selected as steady state species, may be set to zero in the material balances in the model of reacting species. In the latter, a constant activity or concentration for the species concentration selected as solvent may be set and the material balance for the solvent species in the model of the reacting system may be removed. The transport and thermodynamic properties are automatically adapted to account for the existence of a solvent species, which dominates the properties of the fluid.

The concentration of a species in a common reacting system may be assumed to be at steady state, i.e. that its time derivative is zero. This assumption does not imply that concentration is constant in the space dimensions x, y, and z. Therefore, a species at steady state is not removed as an unknown in the system of reacting species. The issue of a solvent is more general. If a system has a solvent with a completely dominating concentration, the concentration of that solvent is not significant altered by the reacting system. The concentration of the solvent can thus be removed as an unknown in the system. However, the solvent concentration is needed to determine the thermodynamic and transport properties of the system, which are accounted for by having the user define the concentration or activity of the solvent.

The automatic generation of a species list and labeling of species concentrations by parsing of reaction formulas in the graphical user interface 300 is very advantageous. Reaction steps may then be easily added to the system 50 and the species list on the species page 320 will be automatically updated accordingly. This enables a user to refine a model by, for example, adding intermediate steps in a reacting system without having to redefine the entire system.

The present invention also provides for an automatic evaluation of all contributions to the consumption or production of a species from reaction rate field 130 for all reactions involving the selected species and displays these contributions in rate expression edit field 350. The automatic generation and displaying, in a graphical user interface, of an editable reaction rate expressions for all contributions involving a specific species is very advantageous.

All of the reaction terms in a mass balance for a single species are assembled. The transport and accumulation of a species is then set equal to its consumption or production in the mass balance. This is generally expressed by the equation below:

$$\frac{\partial c_i}{\partial t} + \nabla \cdot N_i + \sum_j R_{i,j} = 0$$

where $R_{ij}$ denotes the reactions j that species i takes part in.

In addition, the present invention provides for the manual setting of a constant activity, concentration, weight or molar fraction, or partial pressure for a selected species. Lock in kinetic expression box 360 can be checked by a user. The concentration of the selected species may be automatically replaced with a constant value specified by the user everywhere in the reaction rate expressions. The selected species, which is checked using lock in kinetic expression box 360, may also be omitted as an unknown in the model, since its value may be set to a constant manually by a user. The possibility to manually define an activity, partial pressure, or concentration that automatically replaces relevant unknown variables everywhere in rate expressions is novel and advantageous.

The concentration of the locked species does not need to be dominating. Instead, if a certain concentration or activity of a species is known, the concentration of the locked species can be used to investigate a system. The possibility to activate or deactivate the locking of a species concentration (or activity) is very advantageous.

Figure 6:
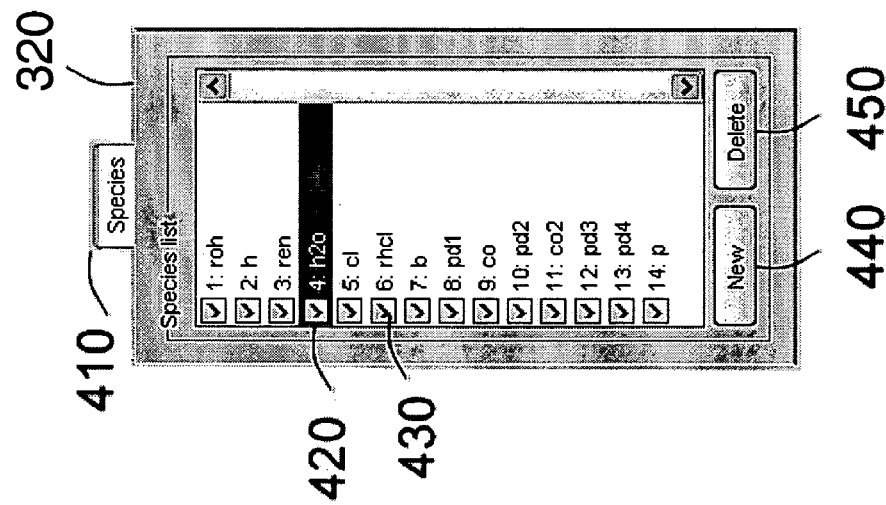
FIG. 6 shows a species list automatically created by the method of the invention from the reaction formula input.

Referring to FIG. 6, the species page 320 is shown in greater detail. The species page 320, also referred to as species list 320, includes a species tab 410, a species selection 420, an active species checkbox 430, a new species button 440, and a delete species button 450. Species tab 410 is clicked by a user to select species page 320, although the species page 320 can include other types and numbers of elements in other configurations. A species may be deactivated by unchecking active species checkbox 430 using a mouse, and the present invention provides for automatic activation and deactivation of species. The deactivated species and the reactions that involve the deactivated species are then removed from the model of the system of reacting species.

The deactivation of a species, implying the removal of the mass balance of that species and its contribution to the energy balance in the system, is a common assumption when modeling a reacting system. It is common that a scientist or an engineer wants to theoretically study a system with and without the presence of a certain species. The possibility to deactivate and activate a species just by checking or un-checking a checkbox is novel and advantageous over methods currently known in the art, which typically require a substantial re-defining of the system for such an assumption.

The present invention also provides for the manual deactivation of a species by a user by unchecking active species checkbox 430. The deactivated species and associated reactions where the species is involved are then eliminated from the model. Another feature of the present invention is that elimination of species can be done automatically by pruning. To do this, a relative value of the concentration of a species is estimated and species having a concentration lower than a specific threshold are automatically eliminated. A user can also manually change the threshold value used in the pruning process. The ability to automatically prune a set of reactions using a threshold, which can be set by the user, gives the user more control and makes the system more efficient.

Box 77, which is shown with dotted lines, represents the fact that reaction list 75 and species list 76 are interconnected, meaning that a change in either of reaction list 75 and species list 76 influences the other and the system 50 will adjust accordingly. Box 77 also represents that "parsing on the fly" is enabled, which implies that a change in an edit field for reaction list 75 or species list 76, for example, by editing step 78, is directly parsed.

In step 81, a reaction rate expression is automatically generated for each of the input formula by system 50. The generated reaction rate expression for the formula in field 110 is illustrated in reaction rate field 130 as shown in FIG. 3. The reaction rate expression may be generated, for example, using the mass action law and the Arrhenius equation by system 50. Reaction rate field 130 can also receive modifications of the reaction type from a user selecting or adjusting the reaction type using the reaction type list box 150 to adjust between reversible, irreversible, or equilibrium reactions, although other types could be selected. If a selection or adjustment is made using box 150 then an automatic change of the reaction delimiter symbol "=>" for irreversible, "<=>" for reversible, and "=" for equilibrium takes place in the system 50. If this occurs, the reaction rate expression in reaction rate field 130 is automatically modified accordingly by the system 50.

Figure 7:
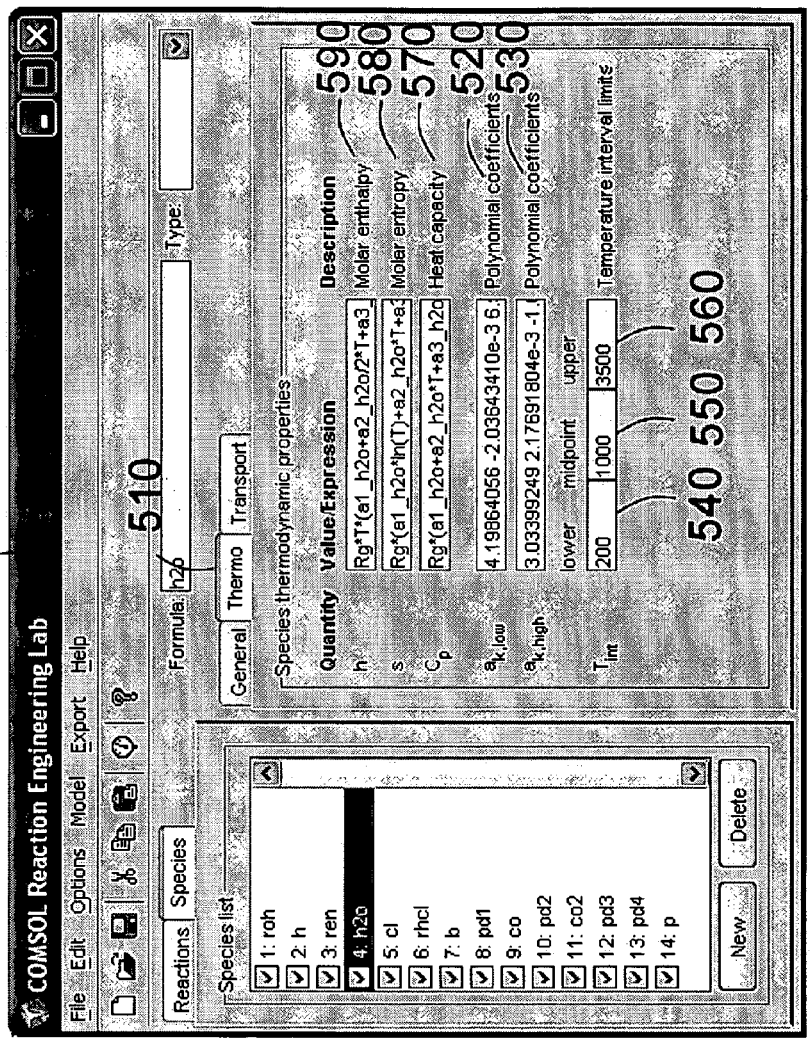
FIG. 7 shows a graphical user interface for inputting polynomial coefficients that the method of the invention uses to generate the thermodynamic properties for the reacting system.

Referring back to FIG. 2, in step 82 the operator has selected a thermodynamic properties tab 510 which causes the system 50 to display a graphical user interface 500 as shown in FIG. 7 in the display system 54. The values on low temperature polynomial coefficient edit field 520, high temperature polynomial coefficient edit field 530, lower temperature limit edit field 540, midpoint temperature edit field 550, and upper temperature edit field 560 may be selected and edited as needed in graphical user interface 500, although graphical user interface 500 can include other types and numbers of elements in other configurations. The expressions for heat capacity may be automatically compiled and displayed in heat capacity field 570. Similarly, molar entropy may be displayed in molar entropy field 580, and molar enthalpy may be displayed in molar enthalpy field 590.

The ability to automatically generate the expressions for thermodynamic properties associated with a species by manual input of polynomial coefficients, expressions generated in an editable form, is very advantageous. The field for the polynomials for the thermodynamic properties is effective as both a displaying field and an editing field.

Figure 8:
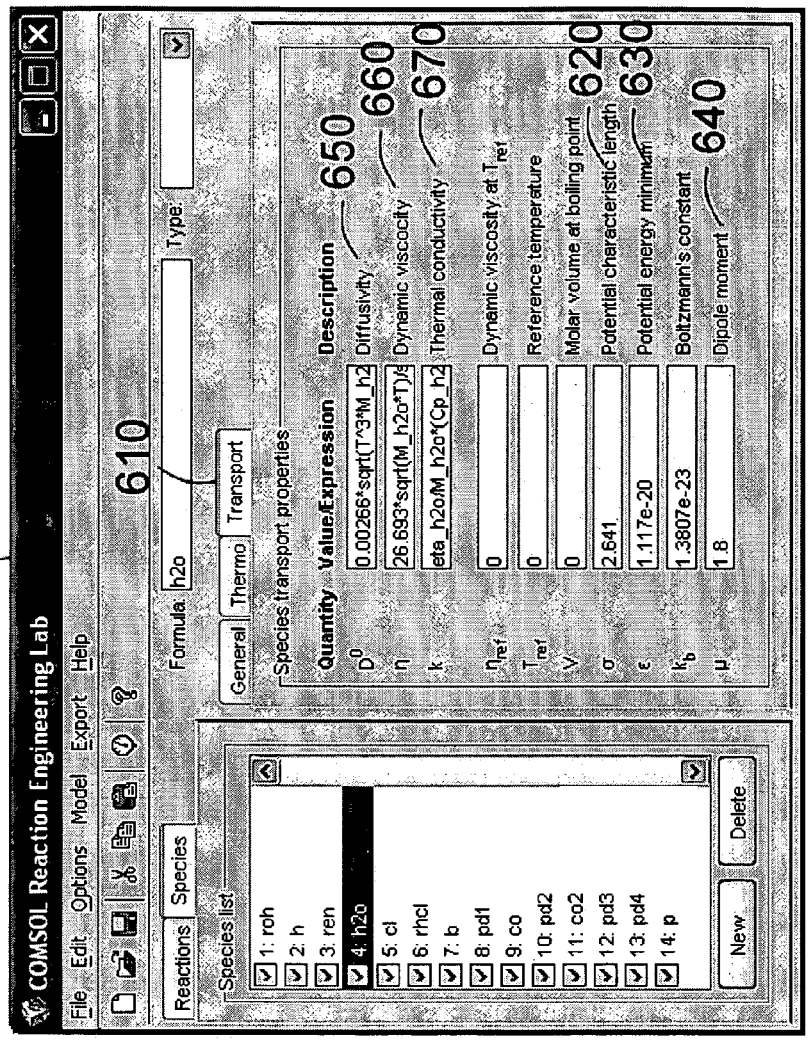
FIG. 8 shows a graphical user interface for inputting physical properties that the method of the invention uses to generate the transport properties of the species in the reacting system.

In step 80, the operator has selected a transport property tab 610 which causes the system 50 to display a graphical user interface 600 as shown in FIG. 8 in the display system 54. A potential characteristic length in characteristic length field 620, a potential energy minimum in potential energy minimum field 630, and a dipole moment for the selected species in dipole moment field 640 can be specified in graphical user interface 600, although other types and numbers of elements in other configurations can be used. In addition, the expressions for molecular diffusivity, thermal conductivity and viscosity may be automatically compiled and displayed in diffusivity field 650, viscosity edit field 660, and thermal conductivity edit field 670, respectively.

Thus, the present invention enables the input of potential characteristic length and potential energy minimum in a graphical user interface, and automatically computes transport properties using Leonard-Jones potential parameters and Stockmayer potential, in an editable form, which is very advantageous. A number of selectable theories for gases and liquids are also supplied in order to calculate transport properties.

Accordingly, in steps 80-82 transport properties, rate expressions, and thermodynamic properties are calculated for each of reaction list 75 and species list 76, as appropriate. As with box 77 described above, box 79 represents the fact that rate expression, thermodynamic properties, and transport properties in steps 80-82 are interconnected, meaning that a change in any of rate expressions, thermodynamic properties, or transport properties in steps 80-82 influences the others, and that "parsing on the fly" is enabled, which implies that a change in an edit field for rate expressions, thermodynamic properties, and transport properties, for example, by editing step 78, is parsed directly.

In step 83, using rate expressions, thermodynamic properties and transport properties, model equations for simulating the system and for representing mass (material) balances, energy balances, and momentum balances are generated by model generating system 53. The resulting equations may be exported at step 84 to a partial differential equations (PDE) solver or to an ordinary differential equations (ODE) solver. The solution of the ODE system shown at step 85 may then be pruned to yield a modified reaction list 75 and species list 76, or may be displayed as a visualization in step 87 of model results.

A typical model of a reacting system includes, for example, a description given by the chemical reaction formulas, the chemical and transport properties of the reactions and species, and a set of model equations. The model equations include, for example, the mass (material), energy, and momentum balances in a reacting system. The reaction rate expressions (also referred to as reaction kinetic expressions) are included as sources or sinks in the mass (material) and energy balances. The user may specify the reaction formula. The reaction rate expressions and the mass and energy balances may then be defined, and the data that will be needed in the model equations may be identified. This may be dependent on modeling assumptions made by a user.

Figure 9:
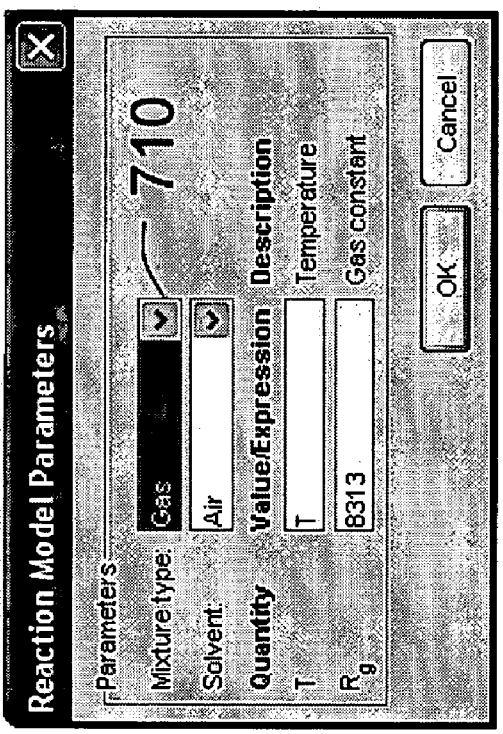
FIG. 9 shows a dialog box for selecting the type of fluid used by the method of the invention to determine thermodynamic and transport properties.

Referring to FIG. 9, a model parameter dialog box 700 which appears in display system 54 is illustrated. Using box 700, the mixture type 710, the solvent, and various quantities, including temperature and the gas constant, may be selected and/or specified. The selections result in automatic changes to the display of graphical user interface 600 to reflect the changes, and the expressions that it displays for transport properties in diffusivity field 650, thermal conductivity field 660 and viscosity field 670. The ability to select different theoretical expressions for transport properties for both gases and liquids in a graphical user interface, in an editable form, is very advantageous.

Figure 10:
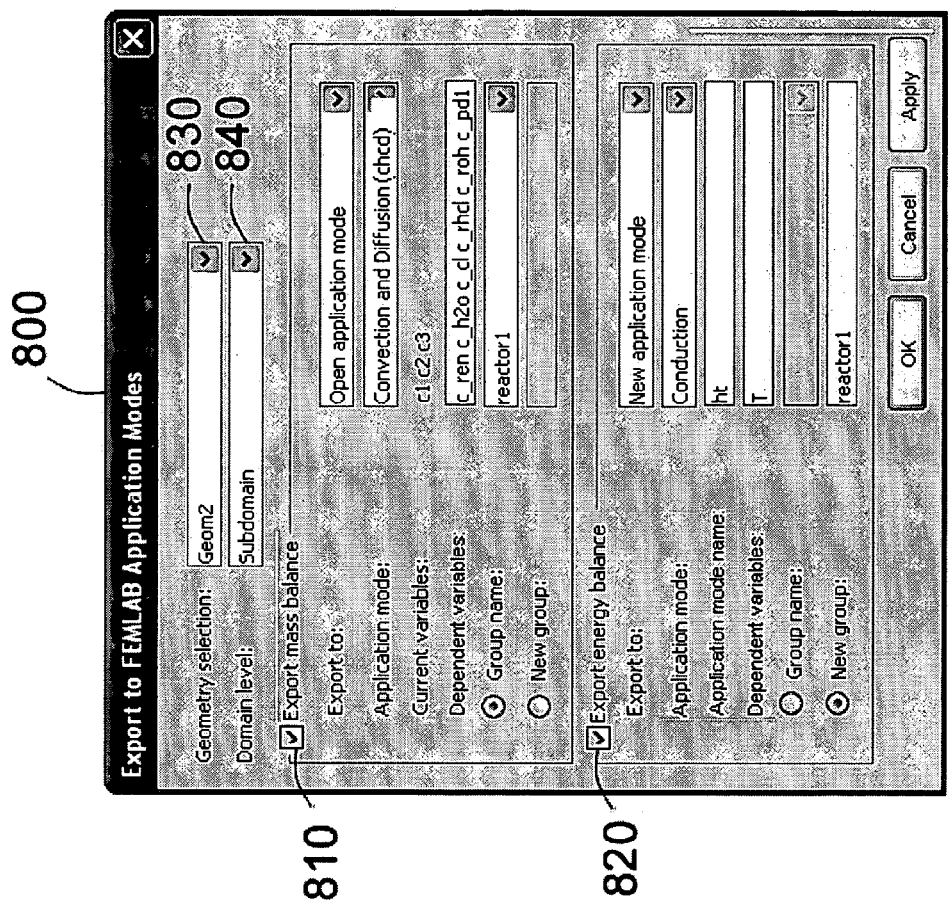
FIG. 10 shows a dialog box used by the system to export a model to a solver of partial differential equations.

Referring to FIG. 10, an export model dialog box 800 which appears in display system 54 and can be utilized to export a model to a program that solves systems of partial differential equations or ordinary differential equations is illustrated. For example, the formulation of the material and energy balances, including reaction kinetics, thermodynamic, and transport properties, may be exported and formulated as a system of partial differential equations. The mass balances or energy balances may be exported separately or together, depending on whether material balance checkbox 810 and energy balance checkbox 820 are selected. The partial differential equations are then automatically formulated in the recipient partial differential equation solver. The system of partial differential equations may also be exported to a specific geometry, defined in the program for solution of partial differential equations, using geometry selection list 830. The system of partial differential equations may also be exported to a specific subdomain, defined in the program that solves partial differential equations, using domain level list 840. The possibility to manipulate the export function and to export interactively in a graphical user interface to a program that solves systems of partial differential equations is novel and very advantageous.

Thus, the present invention provides an automatic method that parses reaction formulas directly typed in to a graphical user interface instead of having to specify these formulas in a data file, of which format can be difficult to penetrate. In addition, the present invention provides an automatic technique for generating the reaction rate expression, associated with each reaction in a set of reaction formulas, instead of having to specify this in a data file. Moreover, the present invention provides that different assumptions about each reaction may be defined in this automatic technique in a graphical user interface and directly display the result of such assumptions instead of having to specify these assumptions in a data file. The present invention further provides automatic elimination of reactions in a reaction list using pruning in a graphical user interface instead of having to use a manual pruning procedure in a data file. Furthermore, the present invention provides a system and method to display the automatically generated reaction rate expressions in a graphical user interface and make these expressions editable instead of having to edit data files.

In addition, the present invention provides automatic generation of a list of species from a set of reaction formulas and to use this list to attribute thermodynamic and transport properties to each species. This may be done by allowing the user to type temperature dependence of the heat capacity in a graphical interface, instead of getting this by loading a data file. Additionally, the present invention provides that the user can define the molecular properties in a graphical user interface, instead of loading it from a data file, to determine the transport properties of a mixture. Moreover, the present invention provides automatic generation of an output file based on the reaction rate expressions and transport properties, which describe the material and energy balances required in a numerical solver of differential equations.

Thus, the present invention further provides a system and method for creating a model for simulating systems of reacting species that allows a user to input a problem by typing a set of reaction formulas directly in to a graphical user interface. In addition, the present invention provides a method that automatically computes the reaction rate expression for each reaction in a reaction list, by parsing the reaction formulas typed by a user directly in to a graphical user interface, wherein the reaction rate expressions may be generated automatically using the mass action law to describe the reaction rate dependence on species concentration. Similarly, the present invention provides a method for computing the reaction rate expression accounting for assumptions regarding reversible, irreversible, and equilibrium reactions, which are used to redefine the previously defined mass action law expressions. The method may use automatic elimination of the equilibrium reaction terms in species balances replacing the eliminated species balances with an equilibrium expression.

In addition, the present invention provides a method for automatic elimination of reactions in a reaction list using a pruning technique. The species and species balances that are considered unimportant, using the relative concentration and relative reaction rates as measure, may be removed from the list of species balances and the reaction expressions for the involved species may be removed in the remaining species balances. The measure and threshold for pruning may use criteria supplied by a user in a graphical user interface.

The present invention also provides a method that includes the representation of the reaction rate expression in an editable form, in a graphical user interface, so that the generation of the reacting species balances is customized to the user's particular needs. The user can then directly change the rate expression by editing directly in a graphical user interface.

Furthermore, the present invention provides a method to obtain thermodynamic data for the involved reactions and species through a graphical user interface. This can be achieved by defining the temperature dependence of the heat capacity of a species by typing it directly into a graphical user interface. The temperature dependence of the free energy, enthalpy, and entropy may then be automatically calculated.

Moreover, the present invention provides a method to obtain transport data for the involved species and mixtures through a graphical user interface. This can be achieved by providing physical constants for dipole moment, Leonard-Jones potential parameters, reference viscosity, reference temperature, and molar volume directly in to a graphical user interface. The molecular diffusivity, thermal conductivity, and viscosity and their temperature dependence may then be automatically calculated.

Also, the present invention provides that a model for simulating systems of reacting species may be exported, directly via a graphical user interface, to a program that solves systems of differential equations.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention.

What is claimed is:

1. A method executed in a computer system including one or more processors and a computer-readable memory, the method comprising:
   generating a model for simulating one or more systems of reacting species, wherein generating the model includes the acts of
      maintaining a list of reaction formulas and at least one selected from the group consisting of a list of reaction rates, a list of species, a list of mass balances, and an energy balance, wherein the at least one of the list of reaction formulas, the list of reaction rates, the list of mass balances, or the energy balance is stored as one or more editable expressions on the computer-readable memory or in a non-transitory computer-readable medium associated with the computer system;
      receiving a reaction formula, the reaction formula being associated with at least one species;
      after receiving the reaction formula, automatically adding the received reaction formula to the list of reaction formulas and automatically updating, using at least one of the one or more processors, the list of species to include species added by the received reaction formula;
      automatically deriving, using at least one of the one or more processors, a reaction rate expression associated with the received reaction formula; and
      automatically updating, using at least one of the one or more processors, the list of mass balances and the energy balance describing the system of reacting species, the automatic updating based on the received reaction formula, the added species, and the derived reaction rate expression,
   wherein the acts of generating the model are implemented prior to transmitting representations of the updated mass balances and energy balance to a solver.

2. The method of claim 1, wherein the received reaction formula is received via a graphical user interface.

3. The method of claim 1, wherein generating the model further includes the act of displaying in a graphical user interface at least one of the updated list of mass balances and energy balance describing the system of reacting species.

4. The method of claim 1, wherein generating the model further includes the act of modifying the derived reaction rate expression via a graphical user interface, such that an update of the list of mass balances and energy balance describing the system of reacting species includes the modified reaction rate expression.

5. The method of claim 1, wherein generating the model further includes the act of displaying the list of reaction formulas in a graphical user interface.

6. The method of claim 1, wherein generating the model further includes the act of eliminating at least one reaction rate expression associated with one or more reactions at equilibrium in the list of reaction formulas.

7. The method of claim 6, wherein the elimination is based on one or more threshold criteria.

8. The method of claim 1, wherein generating the model further includes the act of determining at least one thermodynamic property of each reaction in the list of reaction formulas.

9. The method of claim 1, wherein generating the model further includes the act of determining at least one kinetic property of each reaction in the list of reaction formulas.

10. The method of claim 1, wherein generating the model further includes the act of displaying the list of species in a graphical user interface.

11. The method of claim 1, wherein generating the model further includes the act of determining at least one thermodynamic property for each species in the list of species.

12. The method of claim 1, wherein generating the model further includes the act of determining at least one transport property for each species in the list of species.

13. The method of claim 1, wherein generating the model further includes the act of eliminating at least one time dependent term for at least one species at steady-state.

14. The method of claim 1, wherein generating the model further includes the act of eliminating at least one concentration for at least one species at constant concentration.

15. The method of claim 1, further comprising displaying an output based on the updated list of mass balances and the energy balance describing the system of reacting species, wherein the displayed output includes composition and temperature dependence associated with the system of reacting species.

16. The method of claim 1, further comprising generating mass and energy balances for the reacting species as input for a solver of partial differential equations.

17. The method of claim 1, further comprising:
pruning the list of reaction formulas to deactivate one or more reactions in the list of reaction formulas, the pruning based on one or more criteria;
updating the list of species by removing any species which are no longer part of any reaction in the list of reaction formulas; and
updating the mass balances and energy balance describing the system of reacting species, the updating based at least in part on a removed species.

18. The method of claim 17, wherein the one or more criteria are modified according to user input received via a graphical user interface.

19. The method of claim 1, wherein generating the model further includes the acts of
receiving an edit to one or more of the list of reaction formulas or the list of species;
in response to receiving the edit, automatically updating, using at least one of the one or more processors, an unchanged species in the list of species or an unchanged reaction in the list of reaction formulas; and
generating an updated model for simulating one or more systems of reacting species based on the received edit.

20. The method of claim 1, further comprising:
in response to receiving an edit to one or more of the stored editable expressions of the list of reaction formulas, list of reaction rates, list of mass balances, or energy balance, generating an updated model for simulating one or more systems of reacting species, wherein generating the updated model includes the acts of
automatically updating, using at least one of the one or more processors, one or more of the list of reaction formulas, the list of reaction rates, the list of species, the list of mass balances, or the energy balance to correspond to the edit to the one or more editable expressions; and
automatically deriving, using at least one of the one or more processors, a revised reaction rate expression associated with the received edit.

21. The method of claim 20, wherein generating the updated model further includes the act of automatically updating the list of mass balances and the energy balance describing the system of reacting species based on the revised reaction rate expression.

22. The method of claim 1, wherein generating the model further includes the acts of
receiving an edit to at least one of the list of reaction rate expressions and the list of species;
in response to receiving the edit, automatically updating, using at least one of the one or more processors, an unchanged species in the list of species or an unchanged reaction in the list of reaction formulas; and
generating an updated model for simulating one or more systems of reacting species based on the received edit.

23. The method of claim 1, further comprising transmitting the model to an interface associated with the computer system, wherein the model is configured as input data for a system solving differential equations.

24. A computer system including one or more processors for creating a model for simulating systems of reacting species, the system comprising:
an interface configured to receive user input;
an output interface; and
one or more memory devices, the one or more memory devices including executable instructions, the executable instructions causing at least one of the one or more processors to perform, upon execution, acts comprising generating a model for simulating one or more systems of reacting species, wherein generating the model includes
(a) maintaining a list of reaction formulas and at least one selected from the group consisting of a list of reaction rates, a list of species, a list of mass balances, and an energy balance, wherein the at least one of the list of reaction formulas, the list of reaction rates, the list of mass balances, or the energy balance is stored as one or more editable expressions on at least one of the memory devices or in one or more non-transitory computer readable media associated with the computer system,
(b) receiving a reaction formula, the reaction formula being associated with at least one species,
(c) after receiving the reaction formula, automatically adding the received reaction formula to the list of reaction formulas, and automatically updating the list of species to include species added by the received reaction formula,
(d) automatically deriving a reaction rate expression associated with the received reaction formula, and
(e) automatically updating the list of mass balances and the energy balance describing the system of reacting species, the automatic updating based on the received reaction formula, the added species, and the derived reaction rate expression,
wherein the generating the model is implemented prior to transmitting representations of the updated mass balances and energy balance to a solver.

25. The system of claim 24, wherein the received reaction formula is received via a graphical user interface.

26. The system of claim 24, wherein the executable instructions cause at least one of the one or more processors to perform, upon execution, acts further comprising displaying in a graphical user interface at least one of the updated list of mass balances and energy balance describing the system of reacting species.

27. The system of claim 24, wherein generating the model further includes modifying the derived reaction rate expression via a graphical user interface, such that an update of the list of mass balances and energy balance describing the system of reacting species includes the modified reaction rate expression.

28. The system of claim 24, wherein the executable instructions cause at least one of the one or more processors to perform, upon execution, acts further comprising displaying the list of reaction formulas in a graphical user interface.

29. The system of claim 24, wherein generating the model further includes determining at least one thermodynamic property of each reaction in the list of reaction formulas.

30. The system of claim 24, wherein generating the model further includes determining at least one kinetic property of each reaction in the list of reaction formulas.

31. The system of claim 24, wherein the executable instructions cause at least one of the one or more processors to perform, upon execution, acts further comprising displaying the list of species in a graphical user interface.

32. The system of claim 24, wherein generating the model further includes determining at least one thermodynamic property for each species in the list of species.

33. The system of claim 24, wherein generating the model further includes determining at least one transport property for each species in the list of species.

34. The system of claim 24, wherein generating the model further includes eliminating at least one time dependent term for at least one species at steady-state.

35. The system of claim 24, wherein generating the model further includes eliminating at least one concentration for at least one species at constant concentration.

36. The system of claim 24, wherein the executable instructions cause at least one of the one or more processors to perform, upon execution, acts further comprising displaying an output based on the generated model, the output including composition and temperature dependence associated with the system of reacting species.

37. The system of claim 24, wherein the executable instructions cause at least one of the one or more processors to perform, upon execution, acts further comprising generating mass and energy balances for the reacting species as input for a solver of partial differential equations.

38. The system of claim 24, wherein generating the model further includes eliminating at least one reaction rate expression associated with one or more reactions at equilibrium in the list of reaction formulas.

39. The system of claim 38, wherein the elimination is based on one or more threshold criteria.

40. The system of claim 24, wherein the executable instructions cause at least one of the one or more processors to perform, upon execution, acts further comprising
pruning the list of reaction formulas to deactivate one or more reactions in the list of reaction formulas, the pruning based on one or more criteria;
updating the list of species by removing any species which are no longer part of any reaction in the list of reaction formulas; and
updating the mass balances and energy balance describing the system of reacting species, the updating based at least in part on a removed species.

41. The system of claim 40, wherein the one or more criteria are modified according to user input received via a graphical user interface.

42. The system of claim 24, wherein generating the model further includes
receiving an edit to one or more of the list of reaction formulas or the list of species;
in response to receiving the edit, automatically updating, using at least one of the one or more processors, an unchanged species in the list of species or an unchanged reaction in the list of reaction formulas; and
generating an updated model for simulating one or more systems of reacting species based on the received edit.

43. The system of claim 24, wherein generating the model further includes
receiving an edit to at least one of the list of reaction rate expressions and the list of species;
in response to receiving the edit, automatically updating, using at least one of the one or more processors, an unchanged species in the list of species or an unchanged reaction in the list of reaction formulas; and
generating an updated model for simulating one or more systems of reacting species based on the received edit.

44. The system of claim 24, further comprising:
in response to receiving an edit to one or more of the stored editable expressions of the list of reaction formulas, list of reaction rates, list of mass balances, or energy balance, generating an updated model for simulating one or more systems of reacting species, wherein generating the updated model includes
automatically updating, using at least one of the one or more processors, one or more of the list of reaction formulas, the list of reaction rates, the list of species, the list of mass balances, or the energy balance to correspond to the edit to the one or more editable expressions; and
automatically deriving, using at least one of the one or more processors, a revised reaction rate expression associated with the received edit.

45. The system of claim 44, wherein generating the updated model further includes automatically updating the list of mass balances and energy balance describing the system of reacting species based on the revised reaction rate expression.

46. The system of claim 24, wherein the executable instructions cause at least one of the one or more processors to perform, upon execution, acts further comprising transmitting the model to an interface associated with the computer system, the model being configured as input data for a system solving differential equations.

47. A non-transitory computer readable medium having instructions stored thereon, which when executed by a processor, cause the processor to carry out the step of:
generating a model for simulating one or more systems of reacting species, wherein generating the model includes the acts of
maintaining a list of reaction formulas and at least one selected from the group consisting of a list of reaction rates, a list of species, a list of mass balances, and an energy balance, wherein the at least one of the list of reaction formulas, the list of reaction rates, the list of mass balances, or the energy balance is stored as one or more editable analytical expressions on one or more computer readable memories or in one or more computer readable media;
receiving a reaction formula, the reaction formula being associated with at least one species;

after receiving a reaction formula, automatically adding the received reaction formula to the list of reaction formulas and automatically updating the list of species to include species added by the received reaction formula;

automatically deriving a reaction rate expression associated with the received reaction formula; and automatically updating the list of mass balances and the energy balance describing the system of reacting species, the automatic updating based on the received reaction formula, the added species, and the derived reaction rate expression;

wherein the acts of generating the model are implemented prior to transmitting representations of the updated mass balances and energy balance to a solver.

48. The non-transitory computer readable medium of claim 47, wherein the step of generating the model further includes the act of receiving the reaction formula via a graphical user interface.

49. The non-transitory computer readable medium of claim 47, further comprising instructions for carrying out the step of displaying at least one of the updated list of mass balances and energy balance describing the system of reacting species on a graphical user interface.

50. The non-transitory computer readable medium of claim 47, wherein the step of generating the model further includes the act of modifying the derived reaction rate expression via a graphical user interface, such that an update of the list of mass balances and energy balance describing the system of reacting species includes the modified reaction rate expression.

51. The non-transitory computer readable medium of claim 47, wherein the step of generating the model further includes the act of eliminating at least one reaction rate expression associated with one or more reactions at equilibrium in the list of reaction formulas.

52. The non-transitory computer readable medium of claim 47, wherein the step of generating the model further includes the act of determining at least one thermodynamic property of each reaction in the list of reaction formulas.

53. The non-transitory computer readable medium of claim 47, wherein the step of generating the model further includes the act of determining at least one kinetic property of each reaction in the list of reaction formulas.

54. The non-transitory computer readable medium of claim 47, wherein the step of generating the model further includes the act of eliminating at least one time dependent term for at least one species at steady-state.

55. The non-transitory computer readable medium of claim 47, wherein the step of generating the model further includes the act of eliminating at least one concentration for at least one species at constant concentration.

56. The non-transitory computer readable medium of claim 47, further comprising instructions for carrying out the step of displaying an output based on the updated list of mass balances and energy balance describing the system of reacting species, wherein the displayed output includes composition and temperature dependence associated with the system of reacting species.

57. The non-transitory computer readable medium of claim 47, further comprising instructions for carrying out the step of generating mass and energy balances for the reacting species as input for a solver of partial differential equations.

58. The non-transitory computer readable medium of claim 47, further comprising instructions for carrying out the step of transmitting the model to an interface, wherein the model is configured as input data for a system solving differential equations.

59. The non-transitory computer readable medium of claim 47, wherein generating the model further includes the acts of receiving an edit to one or more of the list of reaction formulas or the list of species;

in response to receiving the edit, automatically updating an unchanged species in the list of species or an unchanged reaction in the list of reaction formulas; and generating an updated model for simulating one or more systems of reacting species based on the received edit.

60. The non-transitory computer readable medium of claim 47, wherein generating the model further includes the acts of receiving an edit to at least one of the list of reaction rate expressions and the list of species;

in response to receiving the edit, automatically updating an unchanged species in the list of species or an unchanged reaction in the list of reaction formulas; and generating an updated model for simulating one or more systems of reacting species based on the received edit.

61. The non-transitory computer readable medium of claim 47, further comprising instructions for carrying out the step of displaying the list of species in a graphical user interface.

62. The non-transitory computer readable medium of claim 47, wherein the step of generating the model further includes the act of determining at least one thermodynamic property for each species in the list of species.

63. The non-transitory computer readable medium of claim 47, wherein the step of generating the model further includes the act of determining at least one transport property for each species in the list of species.

64. The non-transitory computer readable medium of claim 47, further comprising instructions for carrying out the step of displaying the list of reaction formulas in a graphical user interface.

65. The non-transitory computer readable medium of claim 51, wherein the elimination is based on one or more threshold criteria.

66. The non-transitory computer readable medium of claim 47, further comprising instructions for carrying out the steps of:

pruning the list of reaction formulas to deactivate one or more reactions in the list of reaction formulas, the pruning based on one or more criteria;

updating the list of species by removing any species which are no longer part of any reaction in the list of reaction formulas; and updating the mass balances and energy balance describing the system of reacting species, the updating based at least in part on a removed species.

67. The non-transitory computer readable medium of claim 66, further comprising instructions for carrying out the step of modifying the one or more criteria via a graphical user interface.

68. The non-transitory computer readable medium of claim 47, further carrying out the step of:

in response to receiving an edit to one or more of the stored editable expressions of the list of reaction formulas, list of reaction rates, list of mass balances, or energy balance, generating an updated model for simulating one or more systems of reacting species, wherein generating the updated model includes the acts of automatically updating one or more of the list of reaction formulas, the list of reaction rates, the list of species, the list of mass balances, or the energy balance to correspond to the edit to the one or more editable expressions; and automatically deriving, using at least one of the one or more processors, a revised reaction rate expression associated with the received edit.

69. The non-transitory computer readable medium of claim 68, wherein generating the updated model further includes the act of automatically updating the list of mass balances and energy balance describing the system of reacting species based on the revised reaction rate expression.

* * * * *